US012582492B2

(12) United States Patent　　(10) Patent No.:　US 12,582,492 B2
Ansari et al.　　(45) Date of Patent: 　　Mar. 24, 2026

(54) MICROROBOTS FOR NEUROSURGICAL APPLICATIONS

(71) Applicants: Georgia Tech Research Corporation, Atlanta, GA (US); Emory University, Atlanta, GA (US)

(72) Inventors: Azadeh Ansari, Atlanta, GA (US); Kimberly Hoang, Atlanta, GA (US); Tony Wang, Atlanta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 226 days.

(21) Appl. No.: 18/576,163

(22) PCT Filed: Jul. 28, 2022

(86) PCT No.: PCT/US2022/074253
§ 371 (c)(1),
(2) Date: Jan. 3, 2024

(87) PCT Pub. No.: WO2023/010075
PCT Pub. Date: Feb. 2, 2023

(65) Prior Publication Data
US 2024/0366318 A1　　Nov. 7, 2024

Related U.S. Application Data

(60) Provisional application No. 63/226,688, filed on Jul. 28, 2021.

(51) Int. Cl.
*A61B 34/30* 　　(2016.01)
*A61B 34/00* 　　(2016.01)

(52) U.S. Cl.
CPC .............. *A61B 34/30* (2016.02); *A61B 34/25* (2016.02); *A61B 34/72* (2016.02); *A61B 34/73* (2016.02)

(58) Field of Classification Search
CPC ......... A61B 34/30; A61B 34/25; A61B 34/72; A61B 34/73; A61B 90/361; A61B 2090/064; A61B 2090/376
See application file for complete search history.

(56) References Cited

U.S. PATENT DOCUMENTS

| | | | |
|---|---|---|---|
| 8,862,205 B2 | 10/2014 | Park et al. | |
| 2017/0119236 A1* | 5/2017 | Hyde | A61B 5/742 |
| 2021/0220068 A1 | 7/2021 | Kim et al. | |

FOREIGN PATENT DOCUMENTS

KR　　　101709574 B1　　2/2017

OTHER PUBLICATIONS

International Search Report and Written Opinion from Application No. PCT/US2022/074253 dated Nov. 1, 2022.
(Continued)

*Primary Examiner* — Jonathan T Kuo
(74) *Attorney, Agent, or Firm* — TROUTMAN PEPPER LOCKE LLP; Ryan A. Schneider; Dustin B. Weeks

(57) ABSTRACT

An exemplary embodiment of the present disclosure provides a micro-robot comprising a body, a helical ridge disposed on an exterior surface of the body, and at least one end effector coupled to the body. At least a portion of the micro-robot can comprise a magnetic material. The micro-robot can be configured to be inserted into a patient's body. The micro-robot can be further configured to be manipulated via a magnetic stimulus external to the patient's body.

19 Claims, 14 Drawing Sheets

(56)          References Cited

OTHER PUBLICATIONS

Wang, et al., "Bidirectional Microrocker Bots Controlled via Neutral Position Offset," Dec. 18, 2020 https://arxiv .org/abs/2010. 11295v2 (Abstract).

Farhadi. Wireless RF Localization and Communication of Micro-Robots inside the Human 23 Body. May 31, 2018 (May 31, 2018). [Retrieved on Sep. 15, 2022]. https://www.chalmers.se/en/projects/Pages/Wireless-RF-Localization-and-Communication-of-Micro-Robots.aspx.

Schmidt et al. Engineering microrobots for targeted cancer therapies from a medical 24 perspective, Nature Communications, vol. 11, 5618. Nov. 5, 2020 URL:https://doi.org/10.1038/s41467-020-19322-7.

* cited by examiner 152     154

153

130

158

180

350

350

350

MICROROBOTS FOR NEUROSURGICAL APPLICATIONS

CROSS-REFERENCE TO RELATED APPLICATIONS

This application claims the benefit of U.S. Provisional Application Ser. No. 63/226,688, filed on 28 Jul. 2021, which is incorporated herein by reference in its entirety as if fully set forth below.

FEDERALLY SPONSORED RESEARCH STATEMENT

This invention was made with government support under grant/award number DGE-1650044 awarded by the National Science Foundation, grant/award number 5R01HL130619-03, awarded by the National Institutes of Health, and 1R01HL130619-A1, awarded by the National Institutes of Health. The government has certain rights in the invention.

FIELD OF THE DISCLOSURE

The various embodiments of the present disclosure relate generally to medical operations, and more particularly to micro-robotic minimally invasive neurosurgery.

BACKGROUND

Aspects of the disclosed technology improve the capabilities of surgical robots particularly for use in neurosurgery. Despite recent advancements in biomedical robotics, neurosurgery has traditionally been limited to maximally invasive procedures, human error, and linear trajectories for the use of long surgical instruments, microscopes for visualization, and large exposure craniotomies. Additionally, conventional, tethered, neurosurgical robots suffer from bulky footprints, limited clinical applications, inability to maneuver in small working corridors, high costs, and constant repositioning.

Current surgical techniques require removal of intervening healthy and sometimes functional tissue, risking neurologic deficits to remove as much cancerous tissue as possible. Trajectories to deep-seated lesions must be linear, limiting surgical options and working corridors depending on the lesion. Surgical options are particularly inadequate when lesions are within or near the ventricular system (cerebrospinal fluid (CSF)-filled spaces in the center of the brain). State-of-the-art intraventricular endoscopy has made significant strides but remains restricted due to its visualization, end-effectors, and maneuverability. Furthermore, given the risks associated with repeat intervention, tissue sampling is reserved when monitoring disease progression. Clinicians must rely on noninvasive methods such as serial magnetic resonance imaging (MRI) imaging to track tumor response to treatment when tissue sampling remains the gold standard. Tissue sampling for disease progression remains underutilized to date.

Current challenges in micro-robotics include down-scaling, swarm/cooperative behavior (non-controllable attractive force between embedded permanent magnets), as well as no individual addressing of the robots or specific functionality.

Neurosurgical oncology is dictated by high precision requirements, narrow working corridors, and, at times, limited visualization. The medical procedures for neurosurgery have remained limited to linear trajectories and large craniotomies to access benign and malignant tumors throughout the brain. As a result, current surgical techniques are highly invasive and risk damage or removal of any surrounding, healthy tissue.

BRIEF SUMMARY

An exemplary embodiment of the present disclosure provides a micro-robot, comprising a body, a helical ridge, and at least one end effector. The helical ridge can be disposed on an exterior surface of the body. The at least one end effector can be coupled to the body. At least a portion of the micro-robot can comprise a magnetic material. The micro-robot can be configured to be inserted into a patient's body. The micro-robot can be further configured to be manipulated via a magnetic stimulus external to the patient's body.

In any of the embodiments disclosed herein the body can be substantially oblong.

In any of the embodiments disclosed herein at least one end effector can comprise a first end effector comprising a reservoir.

In any of the embodiments disclosed herein the at least one end effector can be configured to store and deliver a therapeutic substance to the patient.

In any of the embodiments disclosed herein the reservoir can comprise a plurality of teeth configured to extract a biological sample from the patient, and a plurality of threads configured to store the biological sample.

In any of the embodiments disclosed herein, the plurality of teeth can form a perimeter, and the plurality of threads can be located inside the perimeter.

In any of the embodiments disclosed herein, the body can comprise a polymer material.

In any of the embodiments disclosed herein, the magnetic material can be coated on at least a portion of the exterior surface of the body.

In any of the embodiments disclosed herein, the magnetic material can comprise nickel.

In any of the embodiments disclosed herein, the magnetic material can comprise a semi-hard magnetic nickel thin film, and the microrobot can be configured to perform a bidirectional stick-slip.

In any of the embodiments disclosed herein, the body can comprise a polymer material and the magnetic material can be disposed in an interior of the body.

In any of the embodiments disclosed herein, the magnetic material can comprise NdFeB.

In any of the embodiments disclosed herein, the helical ridge can be configured to reduce adhesion to a biological tissue inside the patient.

In any of the embodiments disclosed herein, the helical ridge can be configured to cause the micro-robot to move through a fluid inside the patient.

In any of the embodiments disclosed herein, the helical ridge can be configured to tunnel through a tissue of the patient.

In any of the embodiments disclosed herein, the at least one end effector can comprise a drill.

Another embodiment of the present disclosure provides a system comprising a micro-robot and a controller. The controller can comprise a user interface, one or more electromagnetic coils, and circuitry. The one or more electromagnetic coils can be configured to generate a magnetic field within a working area. The circuitry can be configured to modulate one or more of an electrical current, a frequency, and a voltage of the one or more electromagnetic coils responsive to an input to the user interface to manipulate the micro-robot in the patient's body.

In any of the embodiments disclosed herein, the system can further comprise a surgical tool and a delivery cannula. The surgical tool can be configured to bore a cranial hole in the patient. The delivery cannula can be configured to deliver the micro-robot through the cranial hole.

Another embodiment of the present disclosure provides a method of performing a medical procedure comprising: delivering a micro-robot to a first site; controlling the micro-robot to travel to a second site, the second site located in the patient's body; and controlling the micro-robot to perform at least one task.

In any of the embodiments disclosed herein, delivering the micro-robot to the first site can comprise: boring a cranial hole; inserting a delivery cannula into the cranial hole; and translating the micro-robot through the delivery cannula.

In any of the embodiments disclosed herein, controlling the micro-robot to travel to the second site in the patient's body can comprise modulating a magnetic field surrounding the first site and the second site such that the micro-robot performs one or more of: rolling across a tissue surface; tunneling through the tissue surface; and swimming through a fluid.

In any of the embodiments disclosed herein, controlling the micro-robot to perform the at least one task can comprise actuating the at least one end effector to deliver a therapeutic substance.

In any of the embodiments disclosed herein, controlling the micro-robot to perform the at least one task can comprise actuating the at least one end effector to extract a biological sample from the patient and to store the biological sample.

In any of the embodiments disclosed herein, controlling the micro-robot to perform the at least one task can comprise delivering an ultrasonic signal to the micro-robot.

In any of the embodiments disclosed herein, controlling the micro-robot to perform the at least one task can comprise delivering a radiofrequency signal to the micro-robot.

In any of the embodiments disclosed herein, controlling the micro-robot to perform the at least one task can comprise exposing the micro-robot to a chemical stimulus. The micro-robot can be configured to receive and act upon the chemical stimulus.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

DETAILED DESCRIPTION

Figure 1:
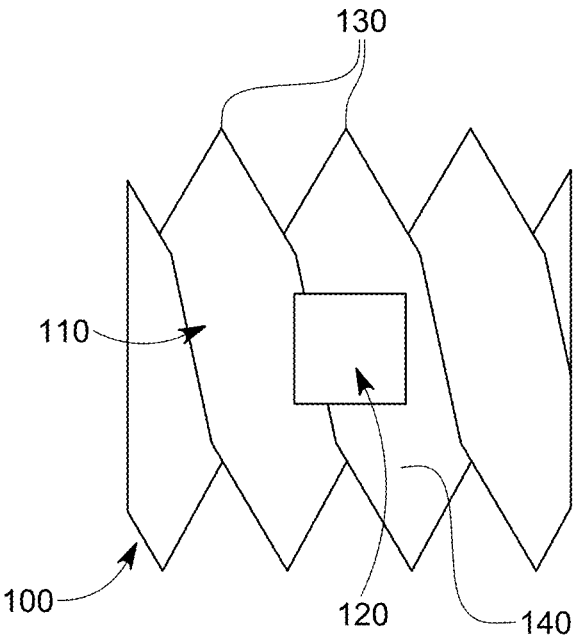
FIG. 1 provides a side view of a microrobot, in accordance with an exemplary embodiment of the present disclosure.

To facilitate an understanding of the principles and features of the present disclosure, various illustrative embodiments are explained below. The components, steps, and materials described hereinafter as making up various elements of the embodiments disclosed herein are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

It must be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms a, an, and the do not denote a limitation of quantity, but rather denote the presence of at least one of the referenced item.

As used herein, the term "and/or" may mean "and," it may mean "or," it may mean exclusive-or," it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Similarly, as used herein, "substantially free" of something, or "substantially pure", and like characterizations, can include both being "at least substantially free" of something, or "at least substantially pure", and being "completely free" of something, or "completely pure."

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

As shown in FIG. 1, an exemplary embodiment of the present disclosure provides a micro-robot (100). The micro-robot can include a body (110), a helical ridge (130) disposed on an exterior surface (140) of the body (110), and at least one end effector (150) (not shown in FIG. 1) coupled to the body (110). At least a portion of the micro-robot (100) can include a magnetic material (120). The micro-robot (100) can be configured to be inserted into a patient's body (200). The micro-robot (100) can be further configured to be manipulated via a magnetic stimulus (300) external to the patient's body (200).

Figure 2:
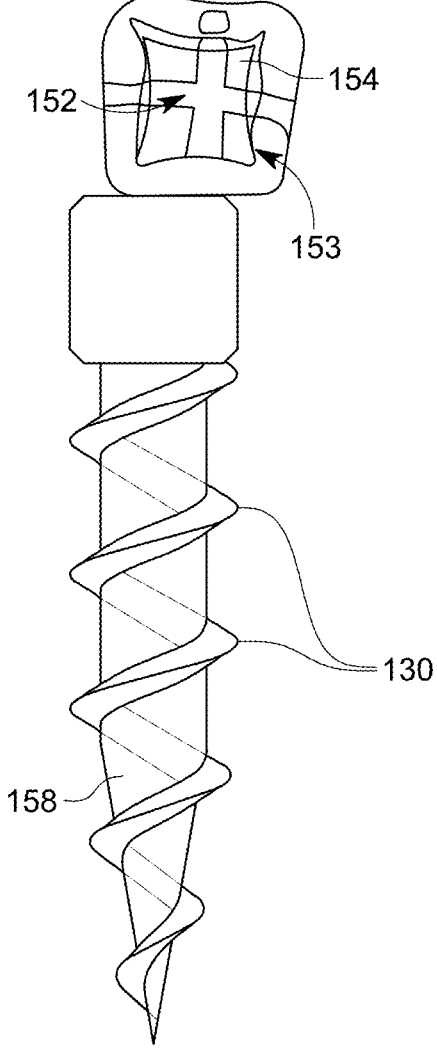
FIG. 2 provides a side view of a microrobot, in accordance with an exemplary embodiment of the present disclosure.

As shown in FIG. 2, in some embodiments, the body (110) can be substantially oblong. Furthermore, in some embodiments, the at least one end effector (150) can include a first end effector 152. The first end effector (152) can include a reservoir (153). Additionally, in some embodiments, at least one end effector (150) is configured to store and deliver a therapeutic substance (154), such as a pharmaceutical drug, to the patient.

Figure 5:
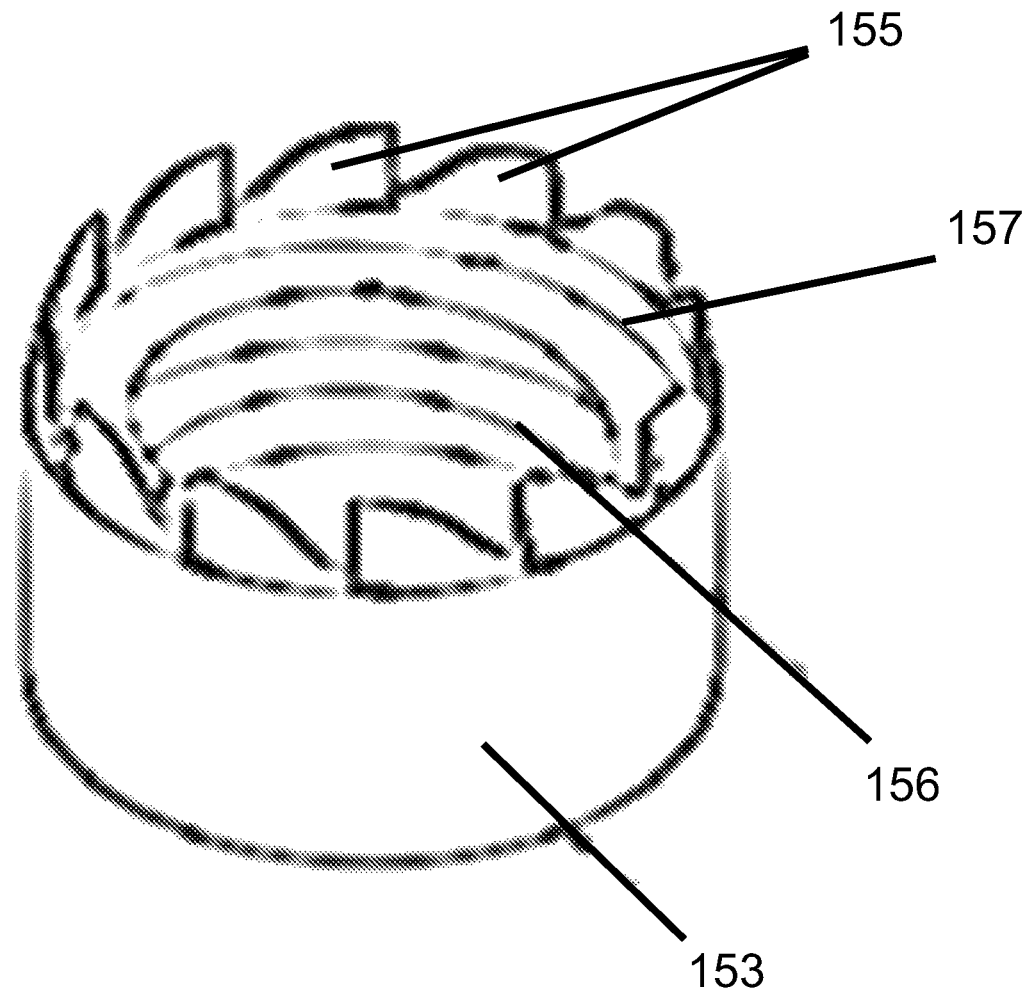
FIG. 5 provides a perspective view of a tissue collecting end effector, in accordance with an exemplary embodiment of the present disclosure.

As shown in FIG. 3A-3C and FIG. 5, in some embodiments, the reservoir (153) can include a plurality of teeth (155) configured to extract a biological sample (210) from the patient and a plurality of threads (156) configured to store the biological sample (210). Furthermore, in some embodiments, as shown in FIG. 5, the plurality of teeth (155) can form a perimeter (157), and the plurality of threads (156) can be located inside the perimeter (157).

Additionally, in some embodiments, the body (110) includes a polymer material (160), and the magnetic material (120) is coated on at least a portion of the exterior surface (140) of the body (110). The polymer material can be many polymer materials known in the art. In some embodiments, the polymer material is a non-magnetic polymer material. The magnetic material can be many magnetic materials known in the art, including, but not limited to, nickel, NdFeB, iron, and the like.

In some embodiments, the body (110) can include a polymer material, and the magnetic material (120) is disposed in an interior of the body (110).

In some embodiments, the helical ridge (130) functions to reduce adhesion to a biological tissue (220) inside the patient.

In some embodiments, the helical ridge is configured to cause the micro-robot to move through a fluid (230) inside the patient.

Figure 3A:
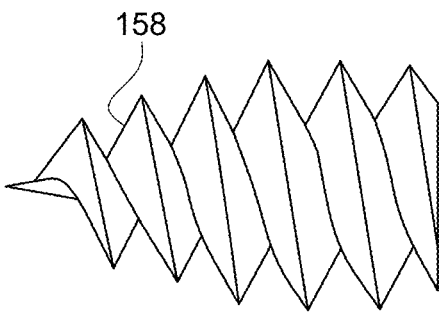
FIGS. 3A-3C provide perspective views of end effectors for use with a microrobot, in accordance with exemplary embodiments of the present disclosure.
Figure 3B:
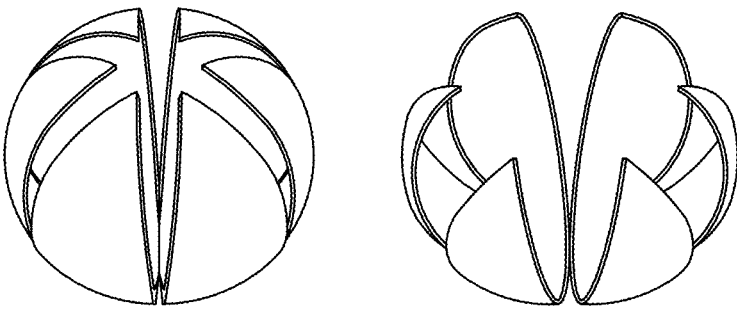
Figure 3C:
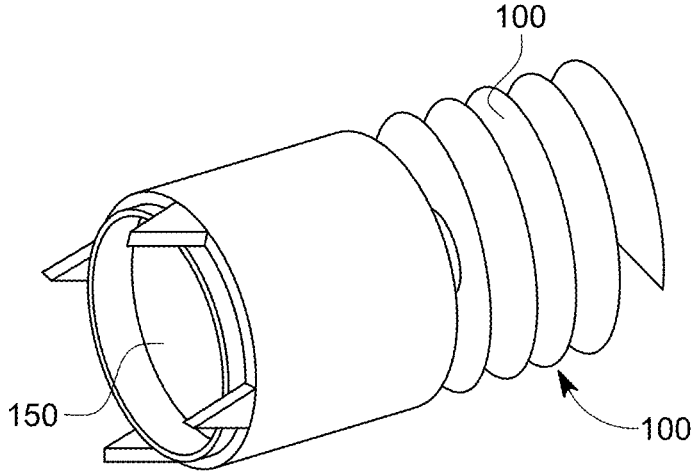
Figure 4:
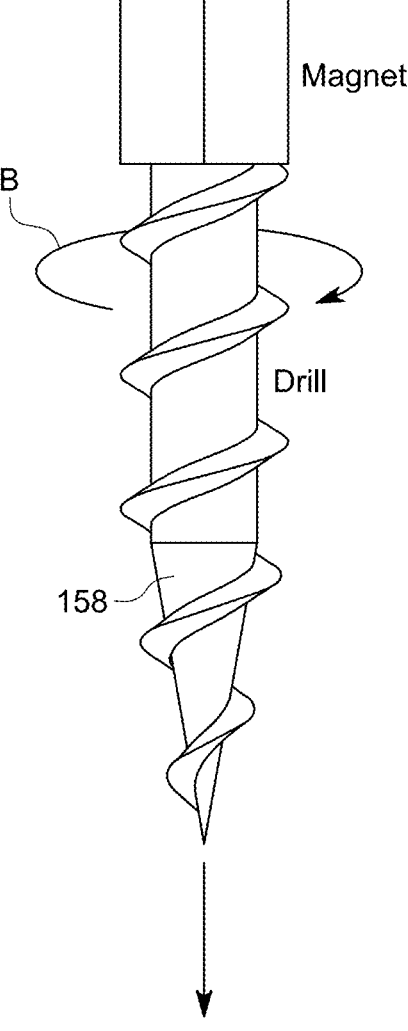
FIG. 4 provides a side view of a micro robot with a drill, in accordance with an exemplary embodiment of the present disclosure.

As shown in FIGS. 3A and 4, in some embodiments, the helical ridge can be configured to tunnel through tissue (230) of the patient, and the at least one end effector comprises a drill (158).

Figure 6A:
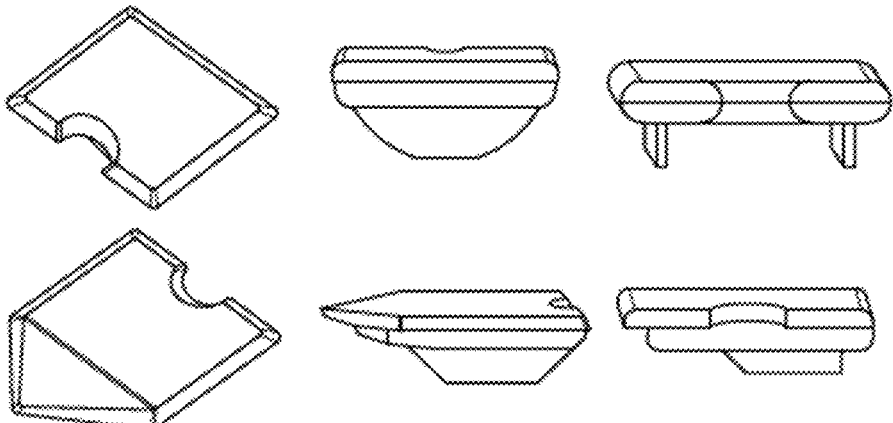
FIGS. 6A-B provide perspective views of a micro-robot, in accordance with an exemplary embodiment of the present disclosure.
Figure 6B:
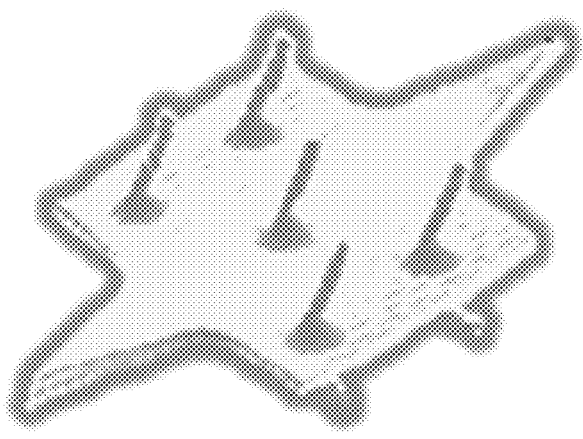

As shown in FIGS. 6A-B, the micro-robots can include various appendages.

Figure 7:
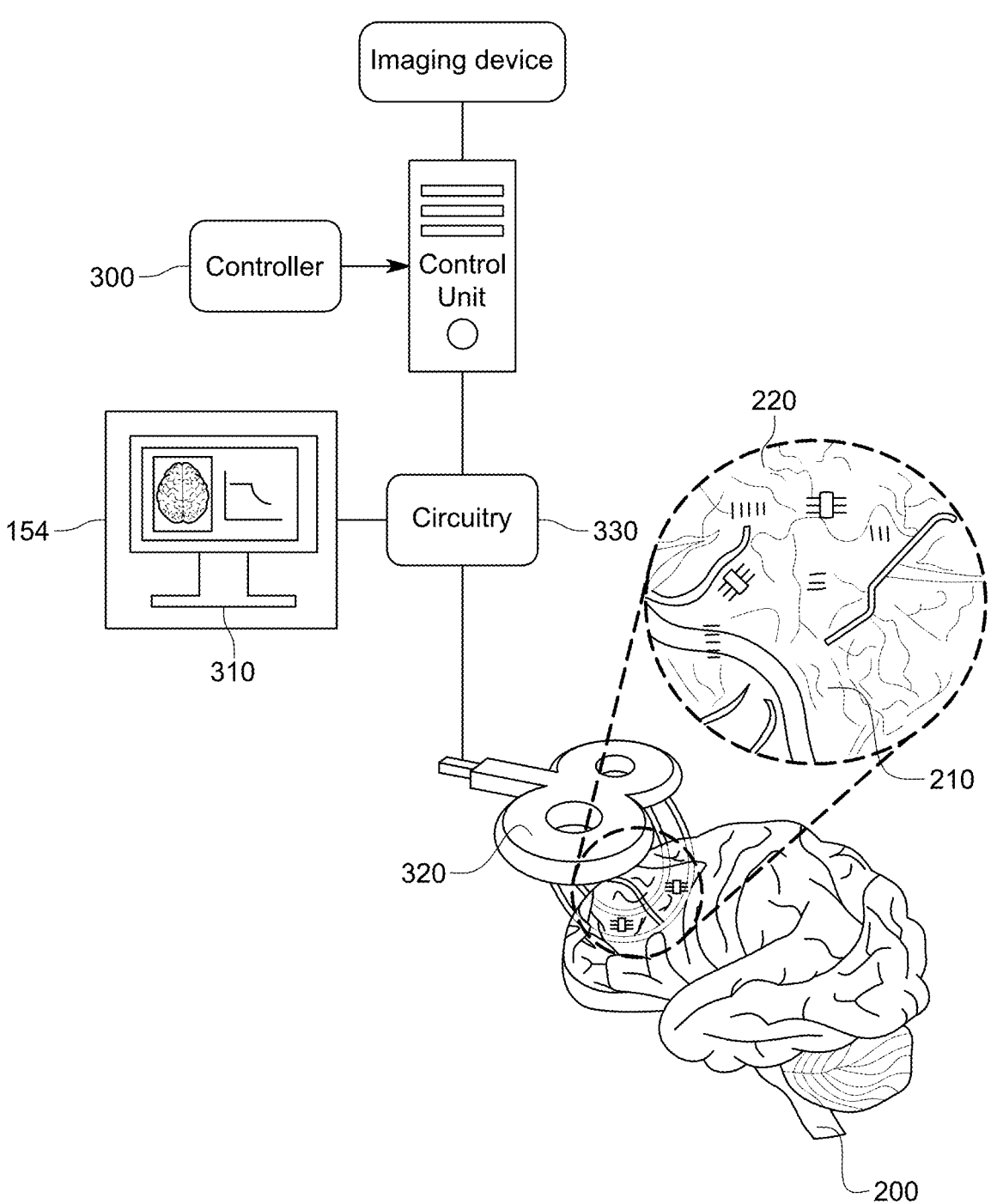
FIG. 7 provides an illustrated diagram of a system, in accordance with an exemplary embodiment of the present disclosure.
Figures 8A, 8B:
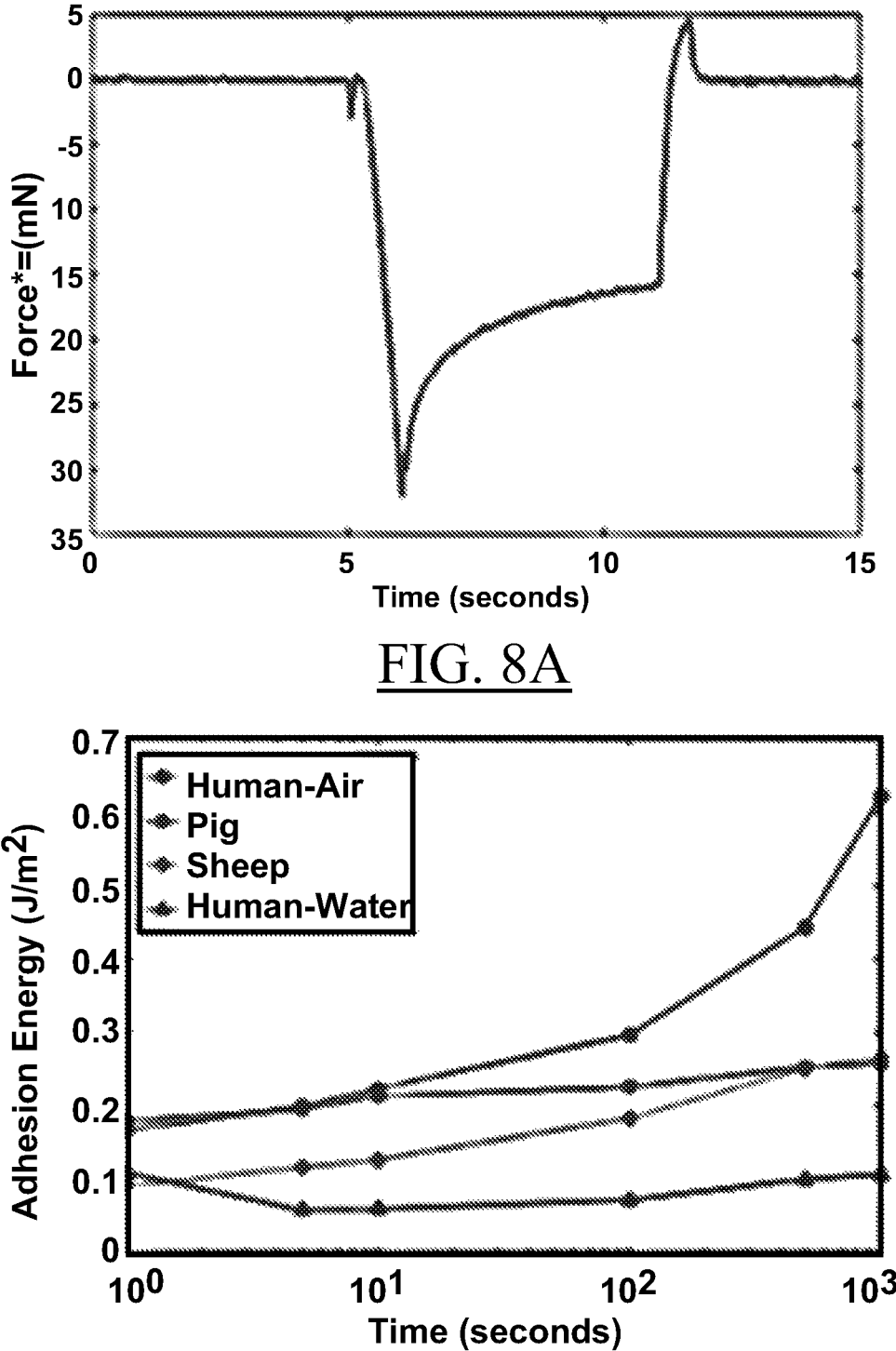
FIG. 8A provides a plot of force on a microrobot versus time when exposed to a magnetic stimulus, in accordance with an exemplary embodiment of the present disclosure.
FIG. 8B provides a plot of adhesion energy of a micro-robot versus time when exposed to a magnetic stimulus, in accordance with an exemplary embodiment of the present disclosure.
Figure 9A:
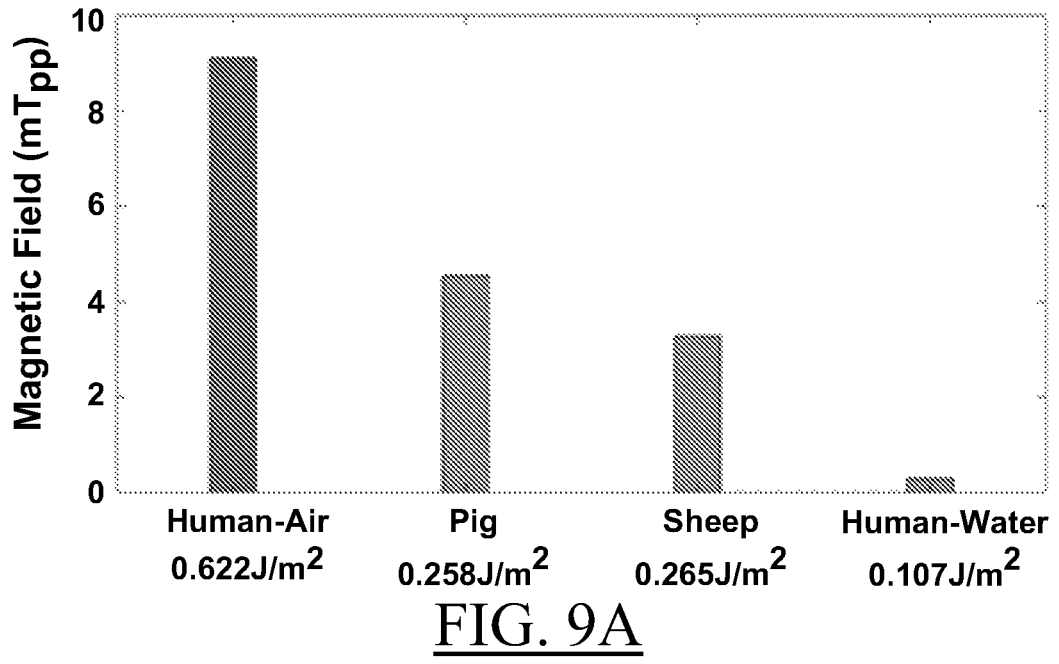
FIG. 9A provides a plot of magnetic field versus adhesion energy in various mediums, in accordance with an exemplary embodiment of the present disclosure.
Figure 9B:
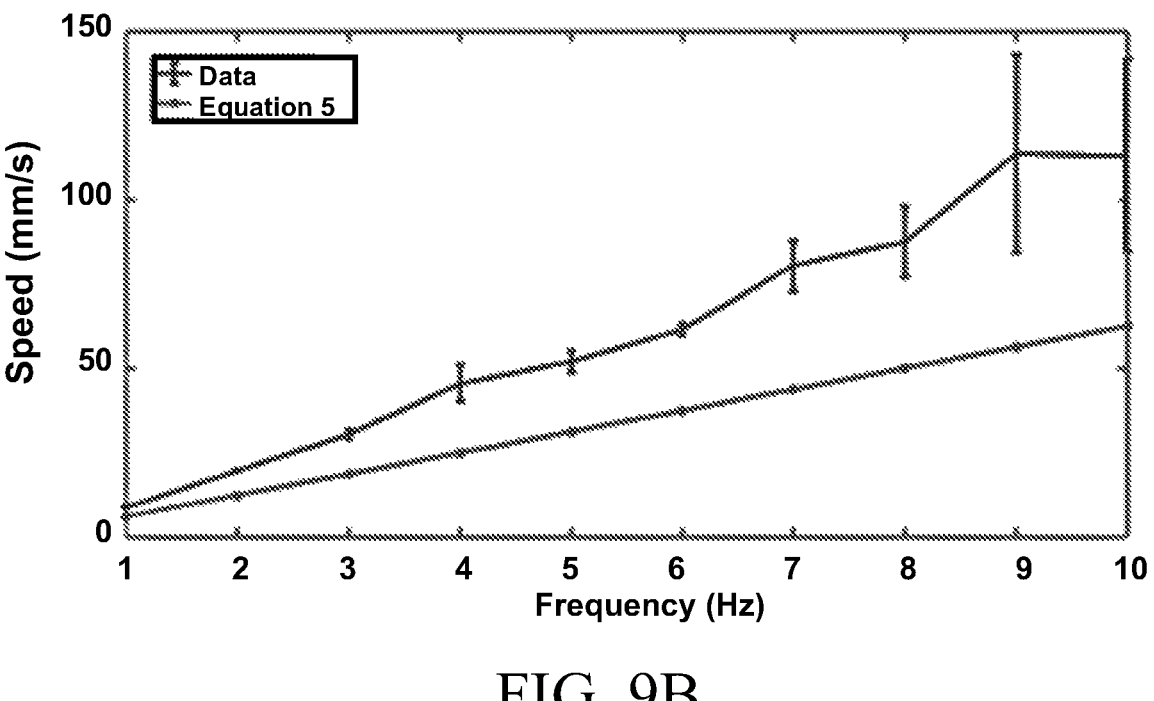
FIG. 9B provides a plot of micro-robot speed versus magnetic field frequency, in accordance with an exemplary embodiment of the present disclosure.
Figure 10A:
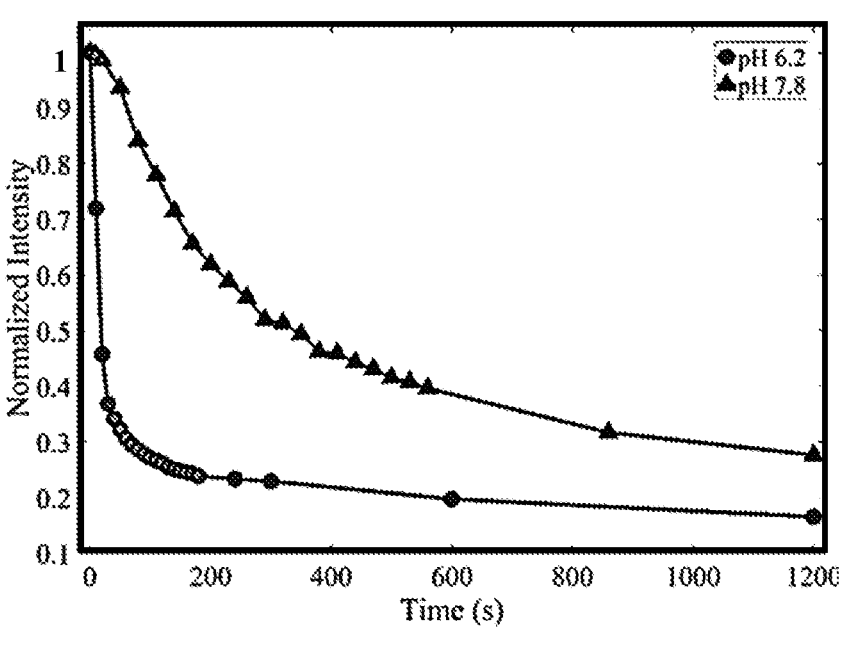
FIG. 10A provides a plot of normalized intensity of a chemical signal versus time, in accordance with an exemplary embodiment of the present disclosure.
Figure 10B:
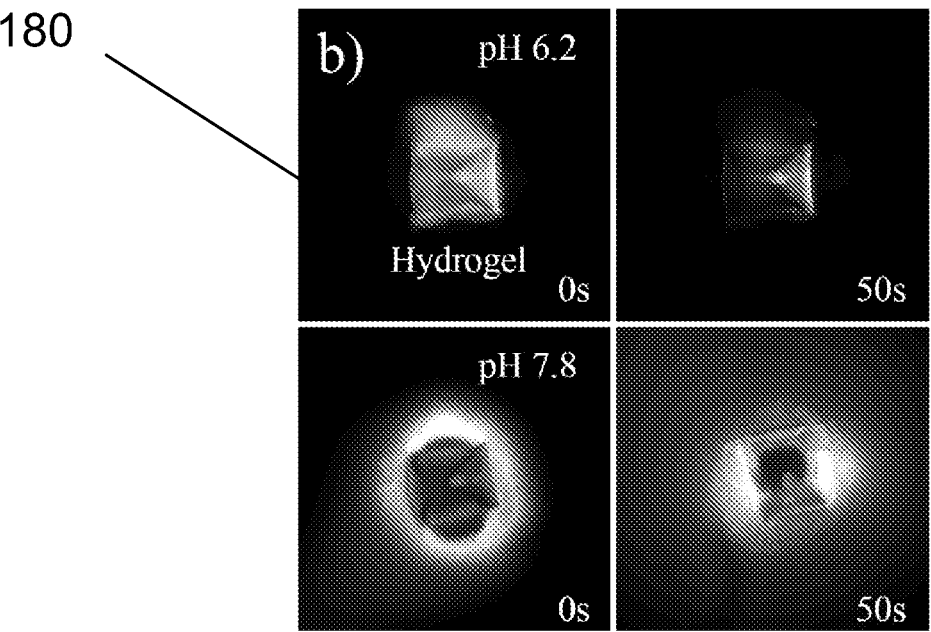
FIG. 10B provides side by side time-lapse views of a hydrogel therapeutic substance delivery end effector in accordance with an exemplary embodiment of the present disclosure.
Figure 11A:
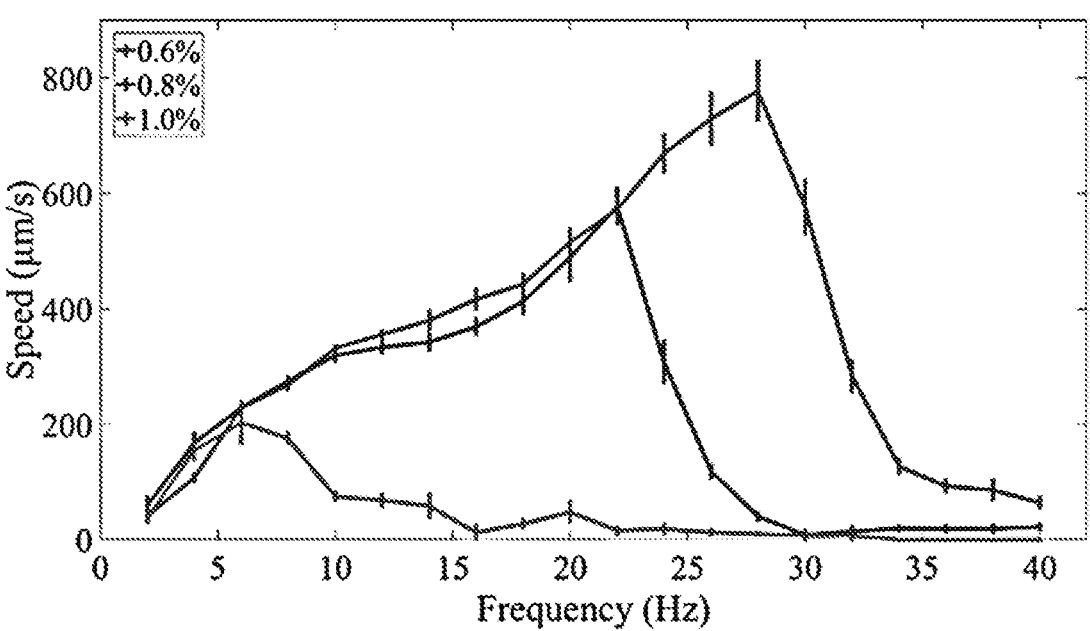
FIG. 11A provides a plot of micro-robot speed versus magnetic field frequency, in accordance with an exemplary embodiment of the present disclosure.
Figure 11B:
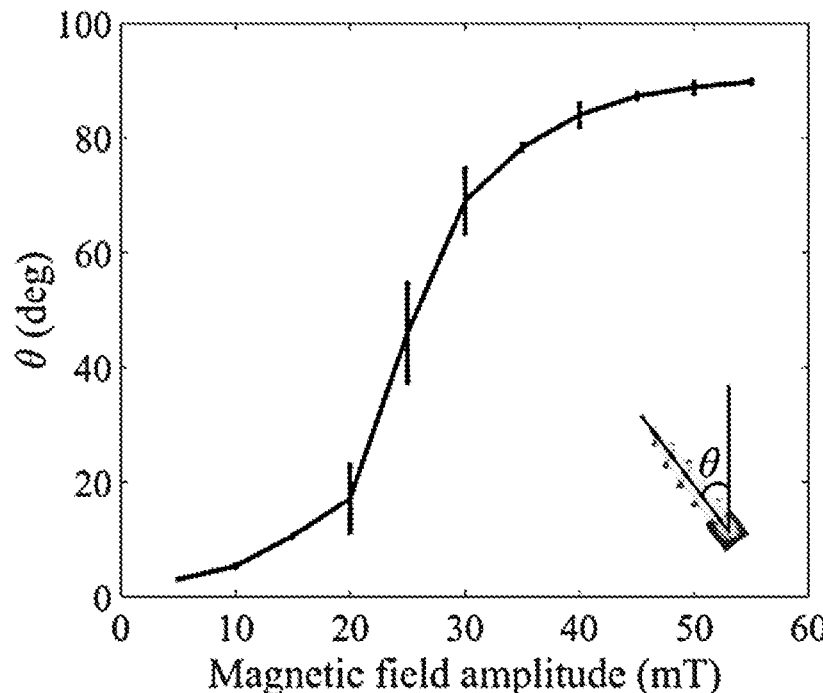
FIG. 11B provides a plot of micro-robot angle versus magnetic field amplitude, in accordance with an exemplary embodiment of the present disclosure.
Figure 12:
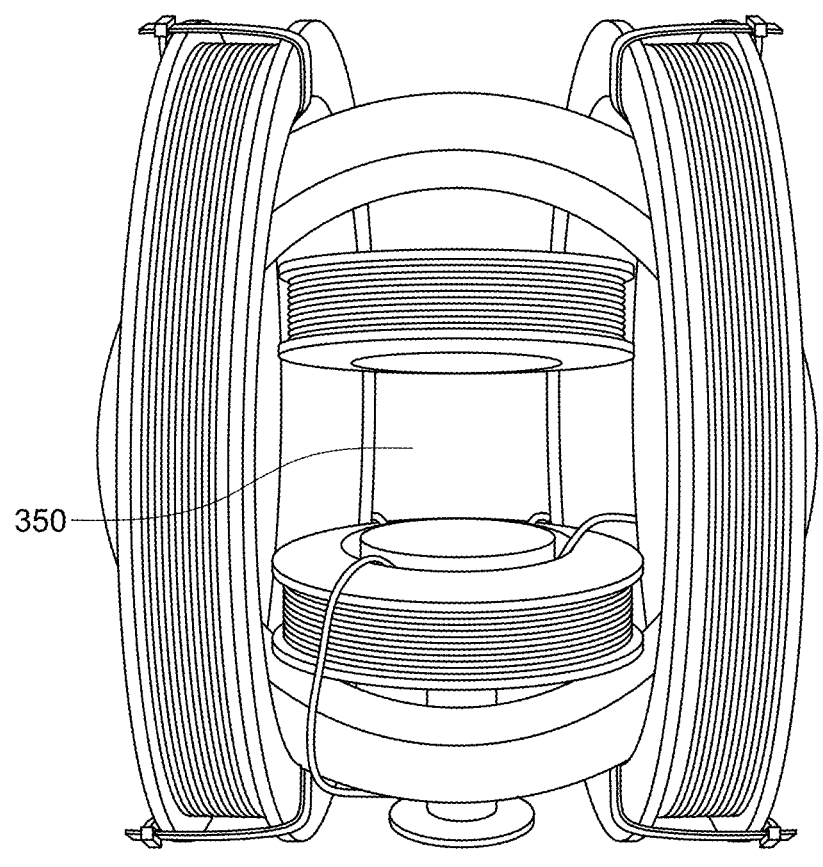
FIG. 12 provides an image of magnetic coils, in accordance with an exemplary embodiment of the present disclosure.
Figure 13A:
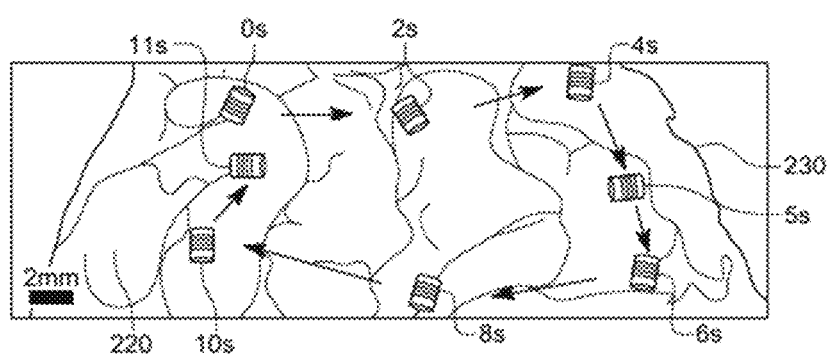
FIGS. 13A-C provide a time lapse view of a micro-robot traversing from a first location to a second location, in accordance with an exemplary embodiment of the present disclosure.
Figure 13B:
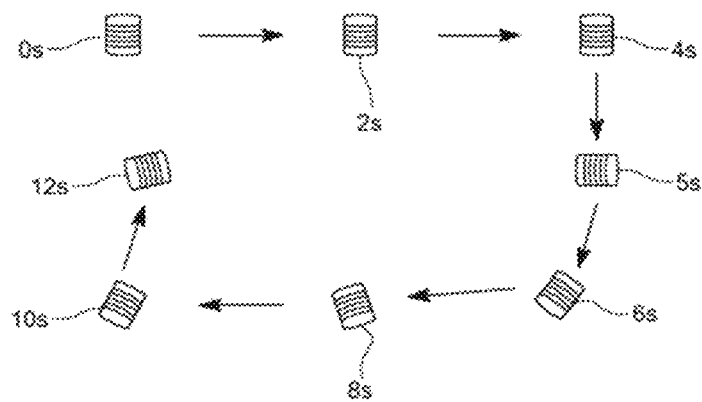
Figure 13C:
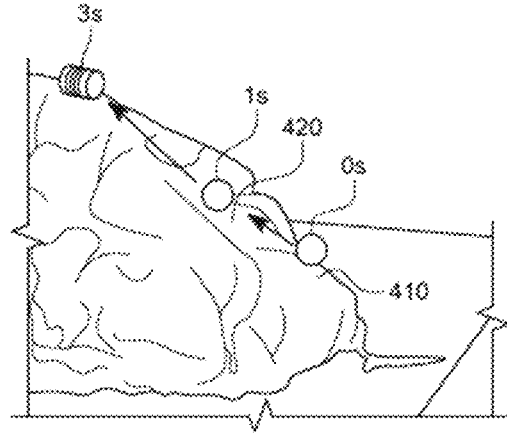
Figure 14:
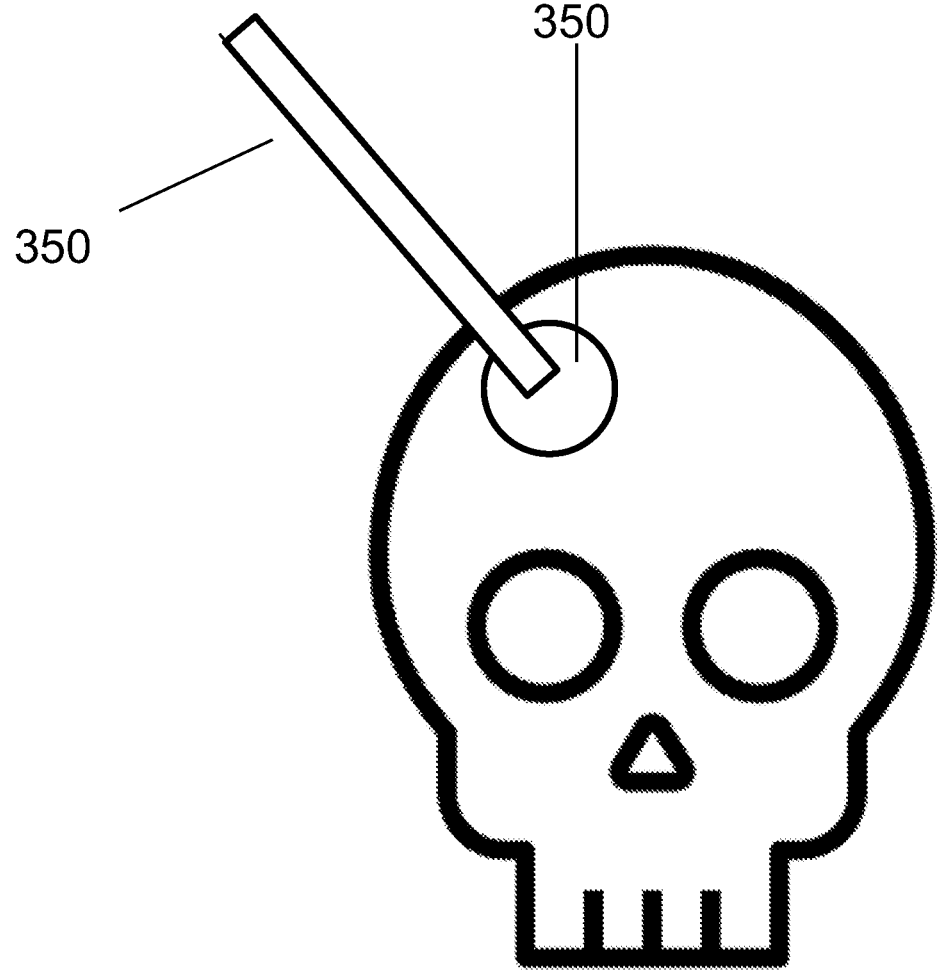
FIG. 14 provides a simplified view of a neurosurgical operation, in accordance with an exemplary embodiment of the present disclosure.

As shown in FIGS. 7 and 12, an exemplary embodiment of the present disclosure provides a system including the micro-robot according to the previously described embodiments, a controller (300) comprising a user interface (310), one or more electromagnetic coils (320) configured to generate a magnetic field within a working area (350), and a circuitry (330) configured to modulate one or more of an electrical current, a frequency, and a voltage of the one or more electromagnetic coils responsive to an input to the user interface to manipulate the micro-robot in the patient's body. Thus, the user interface can permit the user to control the micro-robot via control signals generated by the electromagnetic coils.

In some embodiments, the system can include a surgical tool (340) configured to bore a cranial hole (240) in the patient, and a delivery cannula (350) configured to deliver the micro-robot (100) through the cranial hole (240).

As shown in FIGS. 10B, 13A-C, and 14, another embodiment of the present disclosure provides a method of performing a medical procedure. The method can include delivering the micro-robot disclosed herein to a first site (410), controlling the micro-robot to travel to a second site (420), the second site located in the patient's body, and controlling the micro-robot to perform at least one task.

In some embodiments, delivering the micro-robot to the first site includes boring the cranial hole (240), inserting the delivery cannula (350) into the cranial hole (240), and translating the micro-robot through the delivery cannula.

In some embodiments, controlling the micro-robot to travel to the second site (420) in the patient's body includes modulating a magnetic field surrounding the first site (410) and the second site (420) such that the micro-robot (100) performs one or more of: rolling across a tissue surface (220), tunneling through the tissue surface (220), and swimming through a fluid (230).

In some embodiments, controlling the micro-robot to perform the at least one task includes: actuating the at least one end effector (150) to deliver a therapeutic substance (154).

In some embodiments, controlling the micro-robot to perform the at least one task can include actuating the at least one end effector (150) to extract a biological sample (210) from the patient and to store the biological sample (210).

In some embodiments, controlling the micro-robot to perform the at least one task includes delivering an ultrasonic signal to the micro-robot.

In some embodiments, controlling the micro-robot to perform the at least one task includes delivering a radiofrequency signal to the micro-robot.

In some embodiments, controlling the micro-robot to perform the at least one task includes exposing the micro-robot to a chemical stimulus (180), such as a pH change, and the micro-robot is configured to receive and act upon the chemical stimulus (180).

The following examples further illustrate aspects of the present disclosure. However, they are in no way a limitation of the teachings or disclosure of the present disclosure as set forth herein.

EXAMPLES

Below, exemplary 2 mm long micro-robots are disclosed for complete planar locomotion control over the brain surface via rotational magnetic fields generated by electromagnetic coils. Due to the adhesive properties and unevenness of the brain surface, the micro-robots are designed to be spiral shaped to limit contact to the brain surface.

Additionally, the micro-robot demonstrates climbing capabilities on the brain. This is the first demonstration of micro-robot locomotion on the gyrified brain surface and offers integration with sensors and microsurgical tools. As discussed above, untethered micro-robots have recently attracted significant attention for medical applications due to their extremely small scales and minimally invasive nature. Previous implementations in the medical field include drug/cell delivery, microsurgery, and in vivo imaging/sensing. However, significant effort is still needed to establish micro-robotics as an alternative to conventional medicine. Despite this field showing great potential in synthetic environments such as microfluidic chips or simulated organs, less preclinical work has been done in animal models or ex vivo tissue samples. Significant undefined design challenges remain as micro-robotics transition to medical applications, biologic testing, and preclinical animal models prior to human clinical pilot trials.

In particular, neurosurgery for brain tumors benefits strongly from the usage of micro-robots. Neurosurgical oncology is dictated by high precision requirements, narrow working corridors, and, at times, limited visualization. The medical procedures for neurosurgery have remained limited to linear trajectories and large craniotomies to access benign and malignant tumors throughout the brain. As a result, state-of-the-art surgical techniques can be highly invasive and risk damage or removal of any surrounding, healthy tissue. The minimally invasive nature and fine control of micro-robots would be paradigm shifting for soft tissue microsurgical and oncologic applications.

In some of the embodiments discussed below, the rotating magnetic fields can cause the robot to rotate synchronously and move across the brain. The imaging modality can be computer tomography (CT) or magnetic resonance imaging (MRI). The imaging modality can then give the robot's location to the control unit, allowing for closed loop control.

Currently, the most common actuation mechanisms for micro-robotics include using acoustic/ultrasound, electrical, optical, and magnetic field. Acoustic actuation, despite its compatibility with ultrasound imaging, suffers from low transmission through bone, making both ultrasound imaging and actuation difficult to implement for neurosurgery. Electrical fields typically require the use of a specialized grid for locomotion, which could possibly harm the patient with high voltages. Finally, optical energy transmission necessitates a transparent field of view, which is frequently unavailable for neurosurgery, and the high light intensities required for actuation may unintentionally burn or damage tissue. In contrast, magnetic fields have seen the most success in biomedical applications due to their nonselective permeability through tissue, relative ease of implementation, and strong propulsive forces. These fields are typically generated by current driven electromagnetic coils. By magnetizing and aligning the micro-robot to its desired direction, the coils are able to generate a propulsion force that rotates the robot for motion and navigation.

Geometries for the micro-robots can include: spiral-shaped micro-robots, tissue manipulator micro-robots with a magnetically coated spiral-shaped propeller to engage the tissue for biopsy, micro-grasper robots with prestressed, deposited nickel on silicon dioxide. The spiral-shaped micro-robots and tissue manipulator micro-robots use rotational magnetic fields for motion and tissue manipulation, while the micro-grasper robots uses ON/OFF switching of DC (direct current) magnetic field for on-demand biopsy engagement.

The micro-robots can be actuated magnetically or using ultrasound waves and can navigate on the brain and perform mechanical tasks (e.g. taking biopsy) and/or have sensing capabilities to detect tissue properties such as pressure and stiffness.

The micro-robot can use a spiral-like structure to reduce contact points with the brain tissue, thereby mitigating adhesion forces which can be significant at this scale. It can comprise a 500 pm Neodymium magnet cube embedded inside a 2 mm long polymer matrix, which enables it to be magnetically manipulated. When under a rotating magnetic field, the micro-robot can demonstrate controlled, rotational locomotion on nonorganic and brain substrates. It can also be able to climb inclines to reach targeted areas with good control along desired 2D trajectories. Functionalities such as drilling, pressure sensing, and biopsy taking can be added to the micro-robot.

The micro-robot can resemble a spiral shape to minimize adhesion with the brain surface during rotation. The spiral shape can serve the additional purpose of propulsion through fluid. Owing to their small size, micro-robots in Newtonian fluids, such as cerebrospinal fluid, typically have low Reynolds numbers and experience laminar, smooth flow as well as a greater influence of viscous forces over inertial forces. As a result, swimming consequently requires nonreciprocal, variant motion under time reversal, with examples such as the helical rotation of flagellum in bacteria. The micro-robot can perform swimming and parenchymal tunneling when exposed to rotational magnetic fields configured to mimic this helical movement.

Micro-robots can overcome significant surface forces (adhesion, capillary forces, friction forces) to locomote on brain tissue due to the micromechanics of the brain. Furthermore, the adhesion energy, defined as the amount of energy required to remove contact from the surface, can increase with time and scales proportionally with the contact surface area. To reduce contact area, and therefore adhesion forces, rocker-like appendages can be provided on a 100 μm long micro-robot. Variations of the micro-robot can include a needle micro-robot, and they may be batch fabricated.

Given the size of the relevant brain anatomy, the micro-robot can traverse the gyri/sulci (average gyral width 9-17 mm, average sulcal depth 10 mm). The micro-robots can also move freely within the arachnoid space between parenchyma and dura. The micro-robot can move through parenchyma with minimal tissue disruption. The diameter of biopsy needles can be approximately 0.3-0.4 mm.

The biopsy structure can be made of Nickel or polymers and selectively actuated upon application of rotational and/or DC magnetic field.

The micro-robots can be either nickel-coated 3D (three-dimensional)-printed micro-robots made using two-photon polymerization (2PP) techniques for fabrication of micro-robot with scales <1 mm, as well as molding techniques with embedded permanent magnets for fabrication of micro-robot with—mm scales. The micro-robots can be fabricated via molding based on a model of the micro-robot printed using stereolithography (SLA) with a resolution of 25 pm. Nanoscale 3D printing and subsequent metal deposition can be used to create micro-robots with varying mechanical and magnetic properties.

The nickel-coated 3D-printed polymer pm-scale robots can use "magnetic stepout frequency" together with structural resonance frequency of the micro-robots to selectively actuate the micro-robots to perform cooperative tasks inside the human body.

Alternatively or additionally, fabrication steps of the micro-scale micro-robots can include: a drop of Ip-A photoresist is deposited on an indium-tin oxide glass slide; it is then polymerized in a raster scan via two-photon lithography to print the design; after development in SU08 solution, the robot can be deposited with nickel by thermal metal evaporation.

Alternatively or additionally, fabrication steps for the millimeter scale micro-robots can include: a model is first printed via SLA and cured; the model is placed in molding silicone and heated by hotplate for curing; the model is removed from the cured mold; a 500 μm neodymium magnetic cube is placed and oriented inside the mold by external magnets; UV (ultraviolet) photoresin is poured into the mold and cured; the robot is removed.

Alternatively or additionally, nickel/silicon dioxide hybrid structures can be fabricated by first depositing nickel onto thermally grown silicon dioxide via e-beam evaporation and then releasing the structure by photolithographic patterning and isotropic underetching. The finalized structure bends upwards to form a microgripper structure due to the intrinsic stress gradients in silicon dioxide and nickel films. Here, the radius of curvature can be selectively tuned by annealing treatments of the nickel/silicon dioxide bilayer. Instead of passively cutting tissue, these microgrippers closes under a DC magnetic field along their normal axes to take biopsies.

Fabrication of 2.5-dimensional structures can be achieved using standard lithographic patterning of nickel thin films and intrinsic stress gradients to realize 3D gripper structures that can open and close via magnetic fields.

Neodymium-impregnated soft micro-robots can be molded into a variety of geometries, including spiral robots, rocker robots, and bristle robots. Soft micro-robots have been effective at 1-20 mT (milli Tesla) ranges for movement on the brain surfaces without causing damage to the brain surface. Appendages on the micro-robots can include bristles, fins, blades, and other structures. Nanoscale 3D printing using two photon polymerization (2PP) lithography of micro-robots made of polymer resin, followed by subsequent magnetic thin film, such as nickel, deposition remains an alternative for devices that cannot be successfully molded and require smaller scales. Hard micro-robots have the advantage of higher magnetization, permitting increased movement at the same magnetic field strength compared to their soft counterparts.

The micro-robots can be capable of controllable, bidirectional stick-slip. Adjusting the offset of the waveform input into the electromagnet can tilt the micro-robot either forwards or backwards, which determines the direction of its movement. This motion can arise from the semi-hard magnetic properties of nickel thin films. Additionally, by inputting a DC magnetic field instead of a ramp, the robot can upend on its tip onto the surface. These controls can reduce the number of electromagnetic coils for magnetic manipulation and system bulkiness that can cause patient discomfort.

Bristle micro-robots can utilize stick-slip motion and can provide a secondary alternative to controlled surface locomotion. With a switch to DC current, the current spiral micro-robots utilized for rolling can upend onto the brain surface. Alternation of this DC current can create rotation around the micro-robot's spiral center axis, allowing for minimal screwing motion into the brain surface.

The micro-robots are not limited to the brain, as the precise 3D control married to image guidance in a complex soft-tissue environment can be translated into micro-robotics application for other organs, such as cancer surgery and other surgical areas requiring microskills. This may include fields such as cardiac surgery, vascular surgery, and ophthalmology. The knowledge gained from biopsy performed via untethered surgical robotics is also applicable to other fields of surgical robotics in general. State-of-the-art sensors can be attached to the proposed micro-robots to further increase the functionality of such robots. Sensors can be utilized to measure intracranial pressure, monitor for disease progression, and differentiate cancer. Furthermore, the ability to precisely travel to difficult to reach and deep locations in the brain with multiple micro-robots is ideal for targeted drug delivery. Targeted local drug delivery of chemotherapeutic and systemic therapies to the tumor site in higher concentrations than available via intravenous and/or oral administration can improve survival in this patient population.

The magnetically actuated micro-robots can be capable of stick-slip motion in fluid and biological environments. By modulating the input signal amplitude, phase, and frequency, various modes of micro-robotic motion, such as bidirectional steering, can be achieved with a single compact electromagnetic coil.

The system used for actuation can comprise three electromagnetic coil pairs arranged in a Helmholtz configuration to impose near uniform magnetic fields. Incorporating an imaging module (CT scan/MRI) and a control unit provides closed loop control for the micro-robot. The control system can use machine learning algorithms that minimize human intervention and can utilize a central control unit that keeps track of the micro-robot location. This enables intelligence augmentation in neurosurgery by marrying machine learning algorithms with the physical control/selective actuation of micro-robots. A closed loop system for the micro-robot, imaging, as well as the addition of new functionalities such as drilling and taking biopsies can be utilized.

Regarding the magnetic actuation setup, the magnetic field parameters, such as magnitude, frequency, phase difference and DC offset of each coil, are optimized to induce selective motions in the micro-robots and to selectively engage the biopsy and other function. The magnetic field parameters, such as number of coils, number of turns, threshold input voltage/current, and working distance, are optimized for the various proposed substrates.

The magnetic torque T applied on the robot can be expressed as a function of the magnetic field applied B and its magnetization vector M. In contrast, the force exerted on a magnet $F_m$ can depend on the magnetic gradient present $\nabla B$ instead of the field.

$$T = M * B \qquad (1)$$

$$F_m = M \cdot \nabla B \qquad (2)$$

The main mode of locomotion can be caused by uniform, rotational magnetic fields. In order to move, the micro-robot can overcome its gravitational rest torque $T_g$ expressed as:

$$T_g = \frac{\rho_e g L V_m}{2} \qquad (3)$$

where $T_g$ is the rest torque, L is the robot's major axial length, and g is the gravitational acceleration. Here, $\rho_c$ is the effective density of the robot with density $\rho_r$ when placed in a fluid with density $\rho_f (\rho_c = \rho_r - \rho_f)$. While the gravitation torque can be reduced in fluids denser than air such as cerebrospinal fluid, air can give more conservative estimates of the system. Equation 3 assumes that adhesion is negligible in the system. While this would be nearly true in an environment filled with water or, in the case of the brain, cerebrospinal fluid, a significant amount of air is often introduced intro the cranial cavity with operation/burr hole creation, making it desirable for the micro-bot to be able to move in this environment as well.

To mitigate adhesion, the micro-robot can resemble a spiral for limited contact with the brain surface. The magnetic torque $(T_y)$, magnetic x force $(F_x)$, magnetic z force $(F_z)$, normal force (N), frictional force $(F_{fr})$, and bouyant force $(F_b)$ enable rotational motion and net displacement in the x direction. On the other hand, the linear damping forces (Dx, Dy, and Dz), weight (mg) of the micro-robot, and adhesive pull-off force (P) can act against and impede the motion.

Equations of acting forces on a micro-robot can be characterized by equations 5, 6, and 7 assuming the robot maintains a consistent point of contact.

At microscale, adhesion, friction, and other surface forces can become more relevant than inertial forces such as gravity and therefore require consideration when designing the micro-robots. The pull-off force P for non-Hertzian contact between elastic solids may be expressed as a function of contact radius R and work of adhesion W between the two surfaces.

$$P = \frac{3\pi R W}{2} \qquad (4)$$

Based on equation 8, the pull-off force can scale proportionally with the contact radius of the two surfaces. To mitigate adhesion, the micro-robot to resembles a spiral for limited contact with the brain surface. The magnetic torque $(T_y)$, magnetic x force $(F_x)$, magnetic z force $(F_z)$, normal force (N), frictional force $(F_{fr})$, and bouyant force $(F_b)$ enable rotational motion and net displacement in the x direction. On the other hand, the linear damping forces (Dx, Dy, and Dz), weight (mg) of the micro-robot, and adhesive pull-off force (P) act against and impede the motion.

Equations of acting forces on a microrocker bot can be characterized by equations 5, 6, and 7 assuming the robot maintains a consistent point of contact.

$$mx^{..} = F_x - F_{fr} - D_x \qquad (5)$$

$$mz^{..} = F_z + N + Fb - P - D_z - mg \qquad (6)$$

$$J\ddot{\theta} = T_y + F_{fr}r\sin(\ddot{\theta}) - (N - P)r\cos(\ddot{\theta}) - D_y \qquad (7)$$

where m is the mass, r is the radius of the micro-robot's minor axis, J is the polar moment of inertia of the micro-robot, x" is the acceleration in the x direction, z" is the acceleration in the z direction, $\ddot{\theta}$ is the angle between the embedded magnet poles and the substrate normal vector, and $\ddot{\theta}$ is the angular acceleration.

Each coil can be wrapped with 400 turns of 22 gauge copper wire and is resin coated for fixation. The coil pairs can have radii of 64 mm, 100 mm, and 129 mm with internal resistances of 4.0$\Omega$, 6.7$\Omega$, and 8.9$\Omega$respectively when connected in parallel. This can allow a sample testing bed of approximately 5×5×5 cm.

The actuation frequency can be varied from 1 Hz to 10 Hz in 1 Hz increments.

Given the robot's rotational motion, it can travel its circumferential distance a number of cycles equivalent to the frequency. Therefore, the robot's speed can linearly vary with frequency, as expressed in the following equation:

$$s = 2\pi r f \qquad (8)$$

where s is the speed, r is half the length of the robot's minor axis, and f is the frequency. By taking advantage of the structural resonance of the micro-robots and the dependency of the robot motion on the actuation frequency, more simplified coil setups can be used to induce directional and controllable motion of the micro-robots on the brain surfaces. Three-dimensional control of the robots on complex brain substrates can be achieved by switching between various types of motions (e.g. rolling, swimming) by magnetic field modulation.

Visual tracking via a microscope or camera, as well as CT scans are used to keep track of the position of the individual micro-robots. The three-dimensional position data of the micro-robots on the brain surface is used in the closed-loop system to adjust the magnetic field parameters, such as magnitude, frequency, phase, and DC offset of each coil, for precise motion control as well as the forces the robots exert to the biopsy tissue. The correspondence, or unique identification of each robot, can be maintained by associating detected robots in consecutive frames using Manhattan distance. This allows in-depth analysis of individual robots. In addition, combined information of robots' motion and tissue topology can be compared against motion models acquired from characterization experiments. As a result, different groups of the heterogeneous swarm can be distinguished on the spot without requiring precise placement of robots at the beginning, which greatly simplifies surgeons' operation.

The position can be deduced from real-time CT scan, which can be processed and subsequently fed to the magnetic field parameters. This can be enabled by having various groups of micro-robots that are only responsive to particular frequencies and amplitudes and agnostic to other frequency/amplitudes due to their heterogeneity in mechanical design and magnetic properties.

The heterogeneous robots with different geometries and magnetic properties for brain surgery application collectively can contribute to the effectiveness of the treatments. In particular, two groups of micro-robots, one specializing in cutting and one specializing in transporting the tissues, being controlled simultaneously by the external magnetic field, can maintain individuality by carefully designing the micro-robots' mechanical and magnetic properties and using techniques such as frequency-dependent resonance and step-out. The two groups can be micro-drillers and micro-collectors. The drillers can be designed to rotate under rotational magnetic fields with blades designed around them. Once the target tissue is fragmented, the micro-collectors can collect the fragmented segments and transport them to the area where they are deployed from. The biopsy fragments which resemble in size the standard biopsy fragments obtained with current procedures (~0.2-0.3 cm). These fragments can be collected by cooperative micro-collecting robots to retrieve the tissue pieces for pathology analysis.

Magnetic actuation and control of individual robots and functions within a swarm can be carried out using stepout frequency and structural resonance.

During neurosurgery, it can be desirable for the micro-robots to move freely within the cranial space once a small craniotomy/burr hole (~0.5 cm) is made and the dura is opened for access. To navigate from craniotomy superficial and deep locations, on the brain surface and within the CSF spaces (ventricles), the micro-robots should be able to perform three basic motions: moving on the surface, swimming in CSF, and tunneling through parenchyma. These actions can all be performed in a controlled fashion for precise operations including biopsy.

Sinusoidally driving two pairs of coils with 5 mT and a phase difference of 90 degrees can induce a rotational magnetic field, which can guide the screwbot to rotate about its long axis. By selectively driving the coils, 2D control across the brain surface can be achieved. Additionally, the rotational nature of the screwbot opens up possibilities for drilling through tissue as well as swimming in highly viscous, low Reynolds Newtonian fluids.

The step-out frequency and the dependency of the micro-robot on the magnetic field parameters to selectively actuate robots within a swarm. One of the challenges with magnetic field actuation is the global actuation where all the robots behave the same under a global command. By careful design of the robot geometry (e.g. appendices, cilia, bristles) selective steering of the robots to move in a particular direction by targeting a specific resonance mode of the robot can be achieved.

Due to the uniformity of magnetic fields, different responses can be induced in magnetically driven micro-robots by manipulating their step-out frequencies. If the frequency of the magnetic field surpasses the step-out frequency of a micro-robot, the micro-robot's angular velocity, which can be directly proportional to its velocity, drastically decreases. For a rotating permanent magnet or ferromagnetic ellipsoid, this behavior above the step-out frequency has been solved in closed-form and is characterized by $$\omega_r = \omega_b - \omega_b\left(\sqrt{1 - \left(\frac{\omega_s}{\omega_b}\right)^2}\right) \qquad (9)$$

where $\omega_r$ is the angular frequency of the robot, $\omega_b$ is the magnetic field frequency, and $\omega_s$ is the step-out frequency. When a micro-robot has reached its step-out frequency, it can achieve maximum velocity, and the ratio (R) of its rotational frequency to that of another micro-robot can be equal to $2s^2$ where s is the ratio between the two micro-robots' step-out frequencies. Therefore, by having a step-out frequency 4 times higher that of a baseline robot, the micro-robot may reach speeds 32 times higher. This difference in step-out frequency can be accomplished by varying the geometry and magnetization value of the robots. For the simplest case, a permanent magnet, the step-out frequency is related to the magnetization (m) and magnetic field (h) $\omega_s=\mu_o\|m\| \|h\|/c$, where c is the viscous drag coefficient and $\mu_o$ is the vacuum permeability.

Input information for the control system can be obtained from both an imaging source and the surgeon. To ensure precision in the system, ideally, on-board "trackers" identify the exact location of each micro-robot.

An exemplary user workflow is as follows: (i) path planning on preoperative imaging, (ii) fusing intraoperative imaging to planned path, (iii) performing small burr hole and dural opening for micro-robot deployment, (iv) injecting micro robots into the subdural space (iv) determination of initial position based on new intraoperative imaging, (v) surgeon to adjust planned path given robots starting points and actuation sequence for micro-robots, (vi) micro-robot travel to target with intermittent imaging to confirm accuracy, (vii) surgeon makes necessary adjustments to trajectory, (viii) biopsy of target after confirmation with actuation of distinct functions in different groups of robots (i.e. "micro-drillers" produce tissue sample fragments, and "micro-collectors" pick up the samples), (viii) estimation of the amount of tissue captured during biopsy and termination when the desired amount of sample is acquired, and (ix) micro-robots travel back along path as previously described and removed from the brain. The closed-loop system can handle the actual robot control automatically.

In cases where human intervention may be needed, such as early termination, the surgeons also have the capability to control and retrieve robots manually by programming the electromagnetic coils externally. Safety mechanisms in case of significant errors or unexpected complications that can be managed by manual override can be built into the control system. An additional way to ensure the performance and enhance the integration of the biopsy micro-robot with other procedures in an operation is to link the system directly to other equipment for multimodal input data including endoscopic video feed, complex imaging (ultrasound, preoperative functional imaging, etc), or intraoperative fluorescence. This further reduces imaging registration error and allows for improved targeting of metabolically important tumor regions.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. A micro-robot configured to be inserted into a patient's body comprising:
a body;
a helical ridge disposed on an exterior surface of the body; and at least one end effector comprising a reservoir, the end effector coupled to the body;
wherein the reservoir comprises teeth and threads;
wherein at least a portion of the micro-robot comprises a magnetic material; and
wherein the micro-robot is further configured to be manipulated via a magnetic stimulus external to the patient's body.

2. The micro-robot of claim 1, wherein the teeth are configured to extract a biological sample from the patient; and
wherein the threads are configured to store the biological sample.

3. The micro-robot of claim 2, wherein the body is substantially oblong.

4. The micro-robot of claim 2, wherein the end effector is configured to store and deliver a therapeutic substance to the patient.

5. The micro-robot of claim 2, wherein the teeth form a perimeter; and
wherein the threads are located inside the perimeter.

6. The micro-robot of claim 2, wherein the body comprises a polymer material; and
wherein the magnetic material is coated on at least a portion of the exterior surface of the body.

7. The micro-robot of claim 6, wherein the magnetic material comprises nickel.

8. The microrobot of claim 6, wherein the magnetic material comprises a semi-hard magnetic nickel thin film; and
wherein the microrobot is further configured to be capable of bidirectional stick-slip.

9. The micro-robot of claim 2, wherein the body comprises a polymer material and the magnetic material is disposed in an interior of the body.

10. The micro-robot of claim 9, wherein the magnetic material comprises NdFeB.

11. The micro-robot of claim 2, wherein the helical ridge is configured to reduce adhesion to a biological tissue inside the patient.

12. The micro-robot of claim 2, wherein the helical ridge is configured to cause the micro-robot to move through a fluid inside the patient.

13. The micro-robot of claim 2, wherein the helical ridge is configured to tunnel through a tissue of the patient; and
wherein the end effector comprises a drill.

14. A system comprising:
the micro-robot of claim 1; and
a controller comprising:
a user interface;
one or more electromagnetic coils configured to generate a magnetic field within a working area; and a circuitry configured to modulate at least one of:

an electrical current, a frequency, or a voltage of the one or more electromagnetic coils responsive to an input to the user interface to manipulate the micro-robot in the patient's body.

15. The system of claim 14 further comprising:

a surgical tool configured to bore a cranial hole in the patient; and a delivery cannula configured to deliver the micro-robot through the cranial hole.

16. A method comprising:

controlling the micro-robot of claim 1 to travel to a site located in the patient's body; and controlling the micro-robot to perform at least one task.

17. The method of claim 16, further comprising:

boring a cranial hole; and translating the micro-robot through a delivery cannula at least partially inserted within the cranial hole.

18. The method of claim 16, wherein controlling the micro-robot to perform the at least one task is selected from the group consisting of:

actuating the at least one end effector to deliver a therapeutic substance;

actuating the at least one end effector to extract a biological sample from the patient and to store the biological sample;

delivering an ultrasonic signal to the micro-robot;

delivering a radiofrequency signal to the micro-robot;

exposing the micro-robot to a chemical stimulus, wherein the micro-robot is configured to receive and act upon the chemical stimulus; and combinations thereof.

19. A method comprising:

translating the micro-robot of claim 1 through a delivery cannula to a first site;

modulating a magnetic field surrounding the first site and a second site located in the patient's body such that the micro-robot performs at least one of:

rolling across a tissue surface;

tunneling through the tissue surface; or swimming through a fluid; and controlling the micro-robot to perform at least one task.

\* \* \* \* \*